(12) United States Patent
Sun et al.

(10) Patent No.: US 9,256,712 B2
(45) Date of Patent: Feb. 9, 2016

(54) MEDICAL MONITORING METHOD AND DEVICE INTEGRATING CENTRAL MONITORING FUNCTION

(75) Inventors: Shuo Sun, Shenzhen (CN); Liangkuan Chen, Shenzhen (CN); Zengqiang Zhang, Shenzhen (CN)

(73) Assignee: Edan Instruments, Inc., Shenzhen (CN)

( * ) Notice: Subject to any disclaimer, the term of this patent is extended or adjusted under 35 U.S.C. 154(b) by 743 days.

(21) Appl. No.: 13/582,451

(22) PCT Filed: Oct. 15, 2010

(86) PCT No.: PCT/CN2010/077768
§ 371 (c)(1),
(2), (4) Date: Sep. 3, 2012

(87) PCT Pub. No.: WO2012/048468
PCT Pub. Date: Apr. 19, 2012

(65) Prior Publication Data
US 2012/0331138 A1 Dec. 27, 2012

(30) Foreign Application Priority Data
Oct. 13, 2010 (CN) .......................... 2010 1 0504992

(51) Int. Cl.
*G06F 19/00* (2011.01)
*H04L 12/28* (2006.01)
*A61B 5/00* (2006.01)
*A61B 5/021* (2006.01)
*A61B 5/0402* (2006.01)
*A61B 5/0205* (2006.01)

(52) U.S. Cl.
CPC ............ *G06F 19/3418* (2013.01); *A61B 5/002* (2013.01); *A61B 5/0205* (2013.01); *G06F 19/322* (2013.01); *G06F 19/327* (2013.01); *G06F 19/3406* (2013.01)

(58) Field of Classification Search
None
See application file for complete search history.

(56) References Cited

U.S. PATENT DOCUMENTS

| 5,331,549 A * | 7/1994 | Crawford, Jr. ................. 600/513 |
| 6,731,311 B2 * | 5/2004 | Bufe et al. .................... 715/781 |
| 2002/0013517 A1 * | 1/2002 | West et al. .................... 600/300 |
| 2003/0117296 A1 * | 6/2003 | Seely ....................... 340/870.07 |
| 2003/0187618 A1 * | 10/2003 | Inda et al. ...................... 702/188 |
| 2007/0139421 A1 * | 6/2007 | Chen et al. ..................... 345/501 |
| 2008/0221918 A1 * | 9/2008 | Petersen et al. ................... 705/2 |
| 2010/0298718 A1 * | 11/2010 | Gilham et al. ................ 600/484 |

* cited by examiner

*Primary Examiner* — Ario Etienne
*Assistant Examiner* — Ho Shiu
(74) *Attorney, Agent, or Firm* — Symbus Law Group, LLC; Clifford D. Hyra (57) ABSTRACT

A method for realizing a central monitoring server by using an individual patient monitor device is provided, and the patient monitor device (301) can monitor the patient's physiological parameter and simultaneously can collect and process the data from the other monitor devices through wired or wireless LAN (Local area network). The running state and the patient's information of the other monitors can be looked over on this monitor (301). The monitor (301) can display this monitoring measurement information and simultaneously display all the patients' information of the other monitors which are networked with it, and the other networked monitors can also be controlled by this monitor (301). The monitor (301) can use a single-screen or multi-screen display, and the displaying content can be the same or not.

8 Claims, 6 Drawing Sheets

Fig 7

MEDICAL MONITORING METHOD AND DEVICE INTEGRATING CENTRAL MONITORING FUNCTION This application claims the benefit of Chinese patent application No. 201010504992.3, filed Oct. 13, 2010, which is hereby incorporated by reference in its entirety.

FIELD OF THE INVENTION

The present invention pertains to the category of medical monitoring technology, more particularly it relates to a medical monitoring method and device integrating central monitoring function.

BACKGROUND OF THE INVENTION

Monitors in medical field are mainly used to check and display patient's physiological information in real time. Centrally a monitor includes only one main control board as the central control. There are many parameters used to measure human body signals and each parameter is for one measuring card. The data on these measuring cards is firstly processed by the main control in real-time and then patient's physiological signals are displayed for diagnosis.

The central monitoring server is a network server based on PC platform. Such server runs with a server software under CS or BS. The software can be connected with other monitors via the Ethernet. Consequently all patients' physiological information can be displayed on the monitor and it is easy for doctors to monitor the conditions of all patients at the same time. Meanwhile, doctors can also choose to operate the monitor of one patient through the central station software, e.g. manually starting the blood pressure measurement once. This type of central station server has been widely used in hospitals.

Centrally, one monitor can only display the patient's physiological signal provided by the parameter module of that monitor. A doctor has to use the dedicated central monitoring server if he intends to look through current physiological information of all patients at the same time. At present, some monitors provide the function to look through patient's information of other monitors using the same network, but only one-patient's information can be checked at the same time. In addition, they cannot store patient's physiological information of other monitors, thus it is extremely inconvenient.

DISCLOSURE OF THE INVENTION

In view of the above-described problems, it is one objective of the present invention to overcome the above disadvantages by providing a medical monitoring method and device integrating central monitoring function.

A medical monitoring method integrating central monitoring function provided by the invention may include:

Displaying selection menu of running mode;

Judging user-selected running mode. When user selects central monitoring server mode, broadcast order will be sent to the network terminal and correlative data source will be searched at the network terminal;

When the correlative data source is found, the data source address will be picked up to connect with the terminal of said address so as to obtain the real-time data of said terminal and to place the said real-time data in a data bag.

Analyzing the real-time data in the data bag to obtain the display information;

Displaying the said display information in the form of a menu. When user selects one of the data bags, detailed information of the data bag will be displayed and the terminal corresponding to the data bag will be controlled according to the address information of said data bag.

A medical monitoring device integrating central monitoring function provided by the invention comprises a monitor, a display device and an interactive network equipment.

The said monitor includes:

A measuring unit, used to measure the local data;

A mode selection unit, used to display the running mode selection menu and select the running mode;

A mode judgment unit, connected with the mode selection unit and used to judge the user-selected running mode;

A data receiving/sending unit, connected with the mode judgment unit and the interactive network equipment. When user selects the central monitoring server mode, the broadcast order will be sent to the networked monitor via the interactive network equipment and correlative data source of the monitor will be searched on the network;

A monitor connection unit, connected with the data receiving/sending unit and the interactive network equipment. When the correlative data source is found, the data source address will be picked up via the interactive network equipment to connect with the monitor of said address so as to obtain the real-time data of said terminal and place the said real-time data in a data bag;

A data analysis unit, connected with the data receiving/sending unit and used to analyze the real-time data in the data bag to obtain the display information;

A monitor selection unit, connected with the display device and used to select the target monitor from the display menu;

A monitor operating unit, connected with the monitor selection unit and the interactive network equipment, and used to send an operating instructions to the target monitor via the interactive network equipment;

The said display device and the data analysis unit, which are connected with the monitor selection unit, are used to display the said display information in the form of a menu, and meanwhile, when user selects the data bag from one of the monitors, it will display the detailed information of such data bag.

Advantages

The present invention provides a method achieving central monitoring server via the monitoring device for a single patient. The monitoring device is able to monitor patient's physiological parameters and simultaneously to achieve data collection and data processing functions for other monitoring devices via wired or wireless LAN. In this monitor, doctors can check running status and patient's information of other monitors. The monitor can display the measurement information of itself and display patient's information of all other monitors that are networked with this monitor. It can also control the other networked monitors by this monitor. Single-screen or multi-screen display can be used for this monitor and the display content can be the same or different. LAN display interface and single interface can be quickly switched over for this monitor. This monitor for single patient achieves networking function and it is easy for information viewing and checking Consequently, the processing efficiency is increased and networking costs for the central monitoring server are reduced.

DETAILED DESCRIPTION OF THE EMBODIMENTS

In order to clearly explain the objective, technical solution and advantages of the invention, the invention will be described in further detail below with reference to the attached drawings and embodiments. It should be understood that the specific embodiments are intended to illustrate but not to limit this invention.

Figure 1:
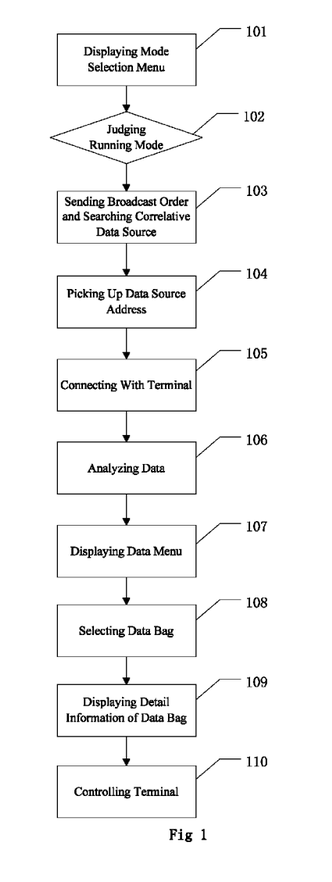
FIG. 1 is a work flow diagram of one example of a medical monitoring method integrating central monitoring function in accordance with the invention.

As shown in FIG. 1, a medical monitoring method integrating central monitoring function provided by the invention may include:

Displaying mode selection menu 101.

A local monitoring device displays a running mode menu in the form of a menu for a user to select;

Judging running mode 102.

The local monitoring device judges the user-selected running mode;

Sending broadcast order and searching correlative data source 103.

When user selects a central monitoring server mode, the local monitoring device is defined as a control terminal monitoring device, used to send broadcast order to the networked controlled terminal and to search correlative data source of the terminal on the network;

Picking up data source address 104.

When the control terminal monitoring device finds the correlative data source, it picks up the said data source address;

Connecting with terminal 105.

The control terminal monitoring device connects with the controlled terminal of the said address to obtain the real-time data of the said controlled terminal and place the said real-time data in a data bag;

Analyzing data 106.

The control terminal monitoring device analyzes the real-time data in the data bag to obtain the display information;

Displaying data menu 107.

The display device displays the display information in the form of a menu;

Selecting data bag 108.

In the display menu, selecting the data-bag data requires to display the detailed information or select the data bag terminal required to be controlled;

Displaying detail information of data bag 109.

The display device displays detailed information of the data bag;

Controlling terminal 110.

The control terminal monitoring device controls the controlled terminal corresponding to the data bag based on the address information of said data bag.

Further, control of the controlled terminal corresponding to the data bag includes: sending control instructions to the controlled terminal corresponding to the selected data bag, said controlled terminal responding to the control instructions, acting to obtain the result data, and then sending the result data to the control terminal monitoring device. Specifically it includes: selecting a specific patient, checking out related information and seting up parameters (e.g. alarm limit setup), or monitoring some patients (e.g. NIBP measurement). The monitor can respond to a special control frame command. When the monitor receives the control frame command sent by another monitor, it responds to the command and then sends the result data to that monitor. The control frame command includes an IP address, a destination IP address and a special command. The special command includes a NIBP measurement command and an alarm limit setup command.

Figure 2:
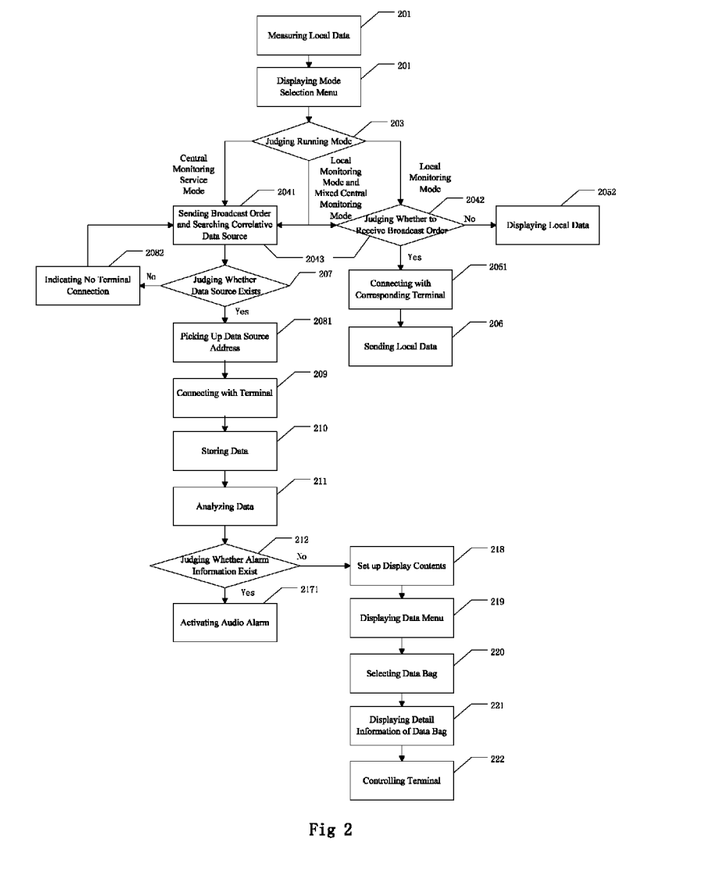
FIG. 2 is a work flow diagram of another example of the medical monitoring method integrating central monitoring function in accordance with the invention.

For the purpose of better understanding, the medical monitoring method integrating central monitoring function provided by the invention will be described in further detail below with reference to an example. As shown in FIG. 2, the medical monitoring method may include:

Measuring local data 201.

The local monitoring device measures various data of the patient under monitoring;

Displaying mode selection menu 202.

The local monitoring device displays a running mode menu in the form of a menu for the user to select;

Judging running mode 203.

The local monitoring device judges the user-selected running mode;

Sending broadcast order and searching correlative data source 2041.

When user selects the central monitoring server mode, the local monitoring device is defined as a control terminal monitoring device, used to send broadcast order to the networked controlled terminal and search correlative data source of the controlled terminal on the network;

Judging whether to receive broadcast order 2042.

When user selects the local monitoring mode, the local monitoring device judges whether the broadcast order is received from the network;

Judging user-selected running mode and whether broadcast order from network is received 2043.

When user selects the mixed mode of local monitoring and central monitoring, the local monitoring device is simultaneously defined as the control terminal monitoring device, used to send broadcast order to the networked controlled terminal, search correlative data source of the controlled terminal on the network and judge whether the broadcast order is received from the network;

Connecting with corresponding terminal 2051.

If the local monitoring device receives the broadcast order, it picks up the original address of the broadcast order and connects with the control terminal monitoring device corresponding to the said address based on the address;

Displaying local data 2052.

If the local monitoring device fails to receive the broadcast order, it reads and displays the local data;

Sending local data 206.

After the local monitoring device connects with the control terminal monitoring device, it sends the corresponding local data to the control terminal monitoring device;

Judging whether data source exists 207.

After the control terminal monitoring device sends the broadcast order to the networked controlled terminal and searches the correlative data source of the controlled terminal on the network, it judges whether data source exists on the network;

Picking up data source address 2081.

When the control terminal monitoring device finds the correlative data source, it picks up the address of the said data source;

Indicating no terminal access 2082.

When the control terminal monitoring device fails to find the correlative data source, it indicates that there is no controlled terminal access. It will resend the broadcast order to the networked controlled terminal and search the correlative data source of the controlled terminal on the network;

Connecting with terminal 209.

After the control terminal monitoring device picks up the data source address, it connects with the controlled terminal of the said address, receives the real-time data from the controlled terminal and places the said real-time data in a data bag. Receiving network data means that when this monitor connects with another monitor, the monitor sends a data bag including target IP address, patient bed No. and real-time information of the patient. This monitor then creates a data buffer area of the corresponding bed based on the above information. The data bag in the buffer area includes patient's physiological information data and alarm data;

Storing data 210.

The control terminal monitoring device stores the real-time data of the data bag and picks up the data bag when user needs to review;

Analyzing data 211.

After the real-time data of the data bag is obtained, the real-time data will be analyzed to obtain the analyzed data information and display information;

Judging whether alarm information exists 212.

The control terminal monitoring device judges whether the alarm information exists in the analyzed data information;

Activating audio alarm 2171.

When the control terminal monitoring device detects that the alarm information exists in the analyzed data information, the preset audio data corresponding to the alarm information will be recalled for alarm;

Set up display content 218.

Set up the display content of every display device and different screens can display the same or different content;

Displaying data menu 219.

The display device displays the display information in the form of a menu;

Selecting data bag 220.

In the display menu, selecting the data-bag data that requires to display detailed information or selecting the data bag terminal that requires to be controlled;

Displaying detail information of data bag 221.

The display device displays detailed information of the selected data bag;

Controlling Terminal 222.

The control instructions sent to the controlled terminal corresponding to the selected data bag by the control terminal monitoring device includes: select a specific patient, check out related information and set up parameters (e.g. alarm limit setup), or monitoring some patients (e.g. NIBP measurement). The monitor can respond to a special control frame command. When the monitor receives the control frame command sent by another monitor, it responds to the command and then sends the result data to that monitor. The control frame command includes an IP address, a destination IP address and a special command. The special command includes a NIBP measurement command and an alarm limit setup command.

Figure 3:
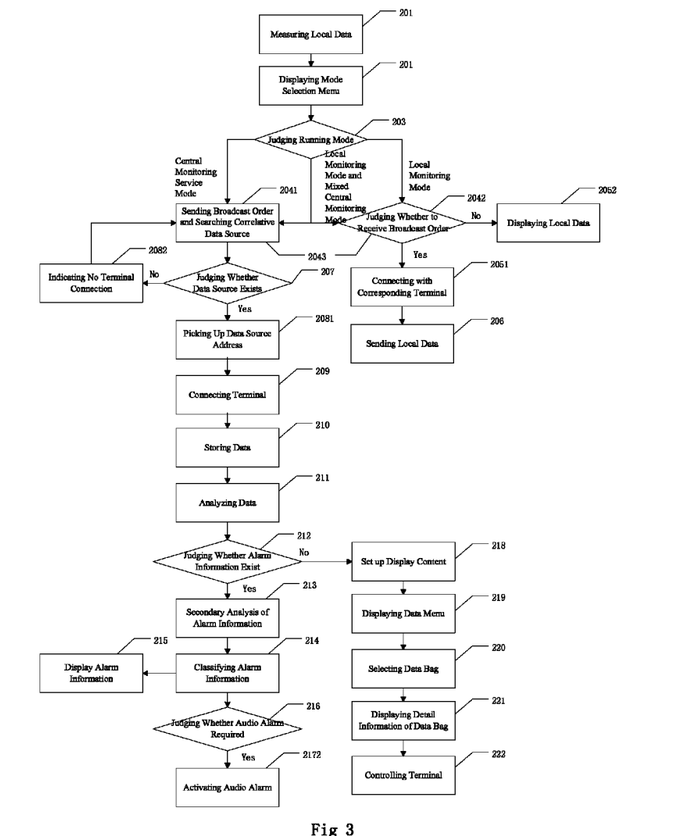
FIG. 3 is a work flow diagram of still another example of the medical monitoring method integrating central monitoring function in accordance with the invention.

For the purpose of better understanding, the medical monitoring method integrating central monitoring function provided by the invention will be described in further detail below with reference to an example. As shown in FIG. 3, the medical monitoring method may include:

Measuring local data 201.

The local monitoring device measures various data of the patient under monitoring;

Displaying mode selection menu 202.

The local monitoring device displays a running mode menu in the form of a menu for the user to select;

Judging running mode 203.

The local monitoring device judges the user-selected running mode;

Sending broadcast order and searching correlative data source 2041.

When user selects the central monitoring server mode, the local monitoring device is defined as a control terminal monitoring device, used to send broadcast order to the networked controlled terminal and search correlative data source of the controlled terminal on the network;

Judging whether to receive broadcast order 2042.

When user selects the local monitoring mode, the local monitoring device judges whether the broadcast order is received from the network;

Judging user-selected running mode and whether broadcast order received from network 2043

When user selects the mixed mode of local monitoring and central monitoring, the local monitoring device is simultaneously defined as the control terminal monitoring device, used to send broadcast order to the networked controlled terminal, search correlative data source of the controlled terminal on the network and judge whether the broadcast order is received from the network;

Connecting with corresponding terminal 2051.

If the local monitoring device receives the broadcast order, it picks up the original address of the broadcast order and connects with the control terminal monitoring device corresponding to said address based on that address;

Displaying local data 2052.

If the local monitoring device fails to receive the broadcast order, it reads and displays the local data;

Sending local data 206.

After the local monitoring device connects with the control terminal monitoring device, it sends the corresponding local data to the control terminal monitoring device;

Judging whether data source exists 207.

After the control terminal monitoring device sends the broadcast order to the networked controlled terminal and searches the correlative data source of the controlled terminal on the network, it judges whether data source exists on the network;

Picking up data source address 2081.

When the control terminal monitoring device finds the correlative data source, it picks up the address of said data source;

Indicating no terminal access 2082.

When the control terminal monitoring device fails to find the correlative data source, it indicates that there is no controlled terminal access. It will resend the broadcast order to the networked controlled terminal and search the correlative data source of the controlled terminal on the network;

Connecting with terminal 209.

After the control terminal monitoring device picks up the data source address, it connects with the controlled terminal of said address, receives the real-time data from the controlled terminal and places said real-time data in a data bag. Receiving network data means that when the local monitor connects with another monitor, the monitor sends a data bag including target IP address, patient bed No. and real-time information of the patient. The local monitor then creates a data buffer area of the corresponding bed based on the above information. The data bag in the buffer area includes patient's physiological information data and alarm data;

Storing data 210.

The control terminal monitoring device stores the real-time data of the data bag and picks up the data bag when user needs to review;

Analyzing data 211.

After the real-time data of the data bag is obtained, the real-time data will be analyzed to obtain the analyzed data information and display information;

Judging whether alarm information exists 212.

The control terminal monitoring device judges whether the alarm information exists in the analyzed data information;

Secondary analysis of alarm information 213.

The remote drive box carries out secondary analysis of the alarm information to obtain the specific alarm content;

Classifying alarm information 214.

When the alarm information contains specific alarm content, the alarm information will be converted into the display information for display and classified according to the preset rules;

Display alarm information 215.

The remote drive box receives the alarm information classification data and the alarm information will be displayed in a descending order based on the classification;

Judging whether audio alarm required 216.

The remote drive box receives the alarm information classification data and judges whether to activate the audio alarm based on the setup;

Activating audio alarm 2172.

When the audio alarm is required, the remote drive box recalls the preset audio data corresponding to the alarm information for alarm;

Set up display content 218.

Set up the display content of every display device and different screens can display the same or different content;

Displaying data menu 219.

The display device displays the display information in the form of a menu;

Selecting data bag 220.

In the display menu, selecting the data-bag data that requires to display detailed information or selecting the data bag terminal that requires to be controlled;

Displaying detailed information of data bag 221.

The display device displays detailed information of the selected data bag;

Controlling Terminal 222.

The control instructions sent to the controlled terminal corresponding to the selected data bag by the control terminal monitoring device includes: selecting a specific patient, checking out related information and setting up parameters (e.g. alarm limit setup), or monitoring some patients (e.g. NIBP measurement). The monitor can respond to a special control frame command. When the monitor receives the control frame command sent by another monitor, it responds to the command and then sends the result data to that monitor. The control frame command includes an IP address, a destination IP address and a special command. The special command includes a NIBP measurement command and an alarm limit setup command.

Figure 4:
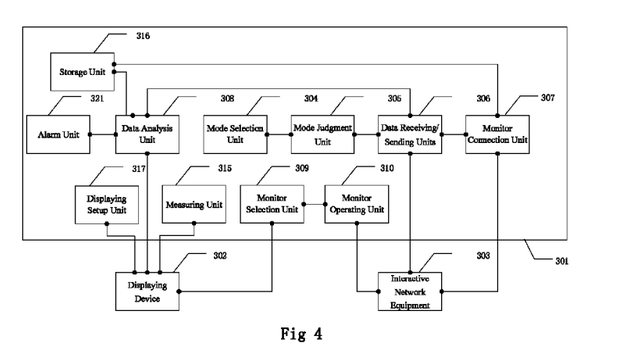
FIG. 4 is a schematic diagram of one example of a medical monitoring device integrating central monitoring function in accordance with the invention.

For the purpose of better understanding, the medical monitoring device integrating central monitoring function provided by the invention will be described in further detail below with reference to an example. As shown in FIG. 4, the medical monitoring device comprises a monitor 301, a display device 302 and an interactive network equipment 303.

The monitor 301 including:

A mode selection unit 304, used to display the running mode selection menu and select the running mode;

A mode judgment unit 305, connected with the mode selection unit 304 and used to judge the user-selected running mode;

A data receiving/sending unit 306, connected with the mode judgment unit 305 and the interactive network equipment 303. When user selects the central monitoring server mode, the broadcast order will be sent to the networked monitor via the interactive network equipment 303 and correlative data source of the monitor will be searched on the network;

A monitor connection unit 307, connected with the data receiving/sending unit 306 and the interactive network equipment 303. When the correlative data source is found, the data source address will be picked up via the interactive network equipment 303 to connect with the monitor of that address so as to obtain the real-time data of said terminal and place said real-time data in a data bag;

A data analysis unit 308, connected with the data receiving/sending unit 306 and used to analyze the real-time data in the data bag to obtain the display information and display information. The data analysis unit 308 analyzes the real-time data and converts it into a standard VGA signal or a DVI signal, a HDMI signal and a DP signal for the display device to display;

A monitor selection unit 309, connected with the display device 302 and used to select the target monitor from the display menu;

A monitor operating unit 310, connected with the monitor selection unit 309 and the interactive network equipment 303, and used to send operating instructions to the target monitor via the interactive network equipment 303;

The display device 302 connected with the data analysis unit 308 and the monitor selection unit 309 is used to display the display information in the form of a menu, and meanwhile, when user selects the data bag from one of the monitors, it will display the detailed information of such data bag.

Further, the monitor 301 also including:

A measuring unit 315, used to measure the local data and send the local data to the display device;

A storage unit 316, connected with the monitor connection unit 307 and the data analysis unit 308, and used to store real-time data and send the real-time data to the data analysis unit 308 when user needs to review;

A display setup unit 317, connected with the display device 302 and used to set up the display content of the display device 302;

An alarm unit 321, connected with the data analysis unit 308. When the alarm information is detected in the analyzed data information, it recalls the preset audio data corresponding to the alarm information for alarm.

Figure 5:
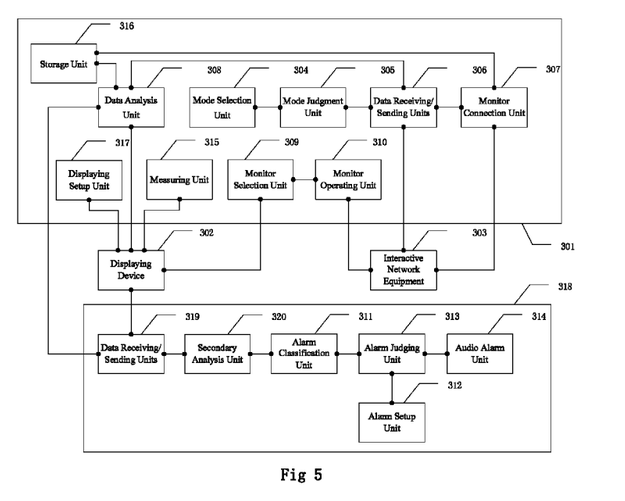
FIG. 5 is a schematic diagram of another example of the medical monitoring device integrating central monitoring function in accordance with the invention.

Further, the medical monitoring device integrating central monitoring function also comprises a remote drive box 318 as shown in FIG. 5.

The remote drive box 318 including:

A data receiving unit 319, connected with the data analysis unit 308 and used to receive the alarm information contained in the analyzed display information and the data information;

A secondary analytic unit 320, connected with the data receiving unit 319 and used to analyze the received alarm information to obtain the specific alarm content;

An alarm processing unit 311, connected with the secondary analytic unit 320. When the specific alarm content is received, the alarm processing unit classifies the alarm information according to the preset rules and then sends it to the display device 32 and an alarm judgment unit 313 in turn in a descending order based on the classification;

The alarm setup unit 312, used to set up the conditions for audio alarm;

An alarm judgment unit 313, connected with the alarm processing unit 311 and the alarm setup unit 312, and used to judge whether the alarm information meets the requirements for audio alarm. The alarm judgment unit 313 then drives an audio alarm unit 314 based on the alarm priority of the patient bed;

The audio alarm unit 314, connected with the alarm judgment unit 313 and used to recall the preset audio data corresponding to the alarm information for alarm when the alarm information meets the requirements for audio alarm.

In this example, the remote drive box 318 is added with an audio alarm drive function. The alarm data includes the alarm classification information and the alarm information. The audio alarm unit 314 recalls the corresponding audio file according to the alarm level to drive the speaker to sound. The alarm level data is connected with the bed information. An operator can set up which bed can sound an alarm. The alarm processing unit deals with several alarms for a single bed and responds to a related alarm based on the alarm priority. Meanwhile, the alarm processing unit converts the alarm information into the display command word, which is inputted into the display drive unit to display the alarm information. With respect to the method to send real-time audio data via network, the method to send the alarm level and alarm message improves the communication efficiency.

Figure 6:
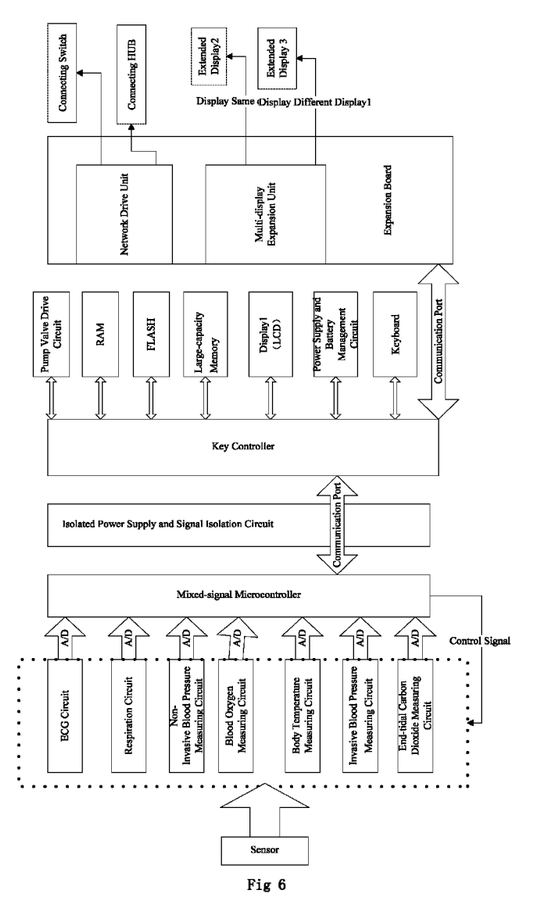
FIG. 6 is a schematic diagram of still another example of the medical monitoring device integrating central monitoring function in accordance with the invention.

For the purpose of better understanding, the medical monitoring device integrating central monitoring function provided by the invention will be described in further detail below with reference to another example. As shown in FIG. 6, the medical monitoring device comprises:

The monitoring device provided by the invention has an independent display and a plurality of sensor interfaces. It can achieve one or more types of the physiological signal monitoring and it has complete keyboard input function and audible/visual alarm function. It also has two or more network ports and two or more Ethernet ports. The monitoring device is equipped with an integrated housing and the whole circuit is located inside the housing. The physiological parameter circuit can choose from ECG circuit, respiration circuit, body temperature circuit, non-invasive blood pressure circuit, invasive blood pressure circuit and end-tidal carbon dioxide monitoring circuit. Those circuits are separately connected with different sensor interfaces. The output is coupled with a front mixed signal processor, which is coupled to a main control unit via the communication port. For example, the front mixed signal processor and the key controller can use ARM series processor or INTER embedded processor. The parameter board and the key control board circuit are isolated by a DC-DC power supply and a communication optocoupler. Therefore the application part isolated from the power supply part. As the application part is connected with the floating ground, patient leakage current is reduced including the number of electric knife for the sensor and influence of defibrillation signal on the main control part. The key control circuit includes RAM, FLASH for storage program and large-capacity memories storing other monitor information such as SATA hardware, IDE hardware and U disk. Ordinary keyboard buttons or touch screen can be used. The audible/visual alarm may use LED for indication and speakers for audio alarm. USB port, multi-network interface and multi-display interface can be expanded for the extended interface. The data/address bus expansion is adopted between the extended interface and the main control board, so that the communication speed is increased. The monitoring device provided by the invention is reserved with two network interfaces with one connected to a router to achieve data connection with other LANs and the other one connected with other monitors to obtain the data thereof via the Ethernet so as to achieve centralized display. The display interface is extended with two routes with one displaying the same information as a main display 1, e.g. use VGA interface to map the monitor information to a bigger size display, and the other one displaying different information with the main display 1. The display content can be set up in the system software. The key controller can place different display content in different display memories and map the different display memories to different displays. When switching the display interface, the main controller still acquires and processes patient's physiological signals.

Figure 7:
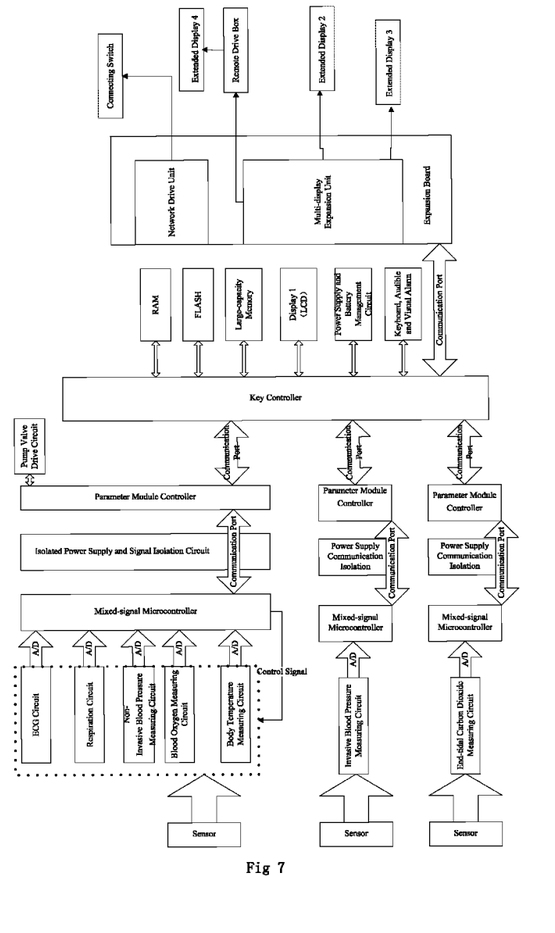
FIG. 7 is a schematic diagram of still another example of the medical monitoring device integrating central monitoring function in accordance with the invention.

For the purpose of better understanding, the medical monitoring device integrating central monitoring function provided by the invention will be described in further detail below with reference to still another example. As shown in FIG. 7, the medical monitoring device comprises:

Based on the previous example, the parameter modularization function is achieved. Those parameter modules are separable from the whole computer. Each parameter module has an independent sensor interface, an isolated power supply and a host computer communication port and is equipped with a separate housing. Those modules are powered by the host computer and the communication methods with the host computer include one or a combination of RS232, RS422, RS485, infrared communication, Bluetooth and wireless. The host computer can work alone when there is no parameter module inserted and it can run as an independent central monitoring server. Those parameter modules may be one or a combination of the parameters of ECG measurement, respiration measurement, body temperature measurement, blood oxygen measurement, non-invasive blood pressure measurement, invasive blood pressure measurement, end-tidal carbon dioxide measurement, anesthetic gas measurement and non-invasive cardiac output measurement. The parameter modules and the whole computer achieve the PNP function. Each parameter module has an independent mixed signal MCU or a dedicated chip. The main function of the module controller is to communicate with the front processor circuit, reprocess the data and convert into the identifiable data format by the host computer so as to communicate with the host computer. The module controller normally uses MCU or FPGA/CPLD as the control bearer.

In this example, the remote drive box of the medical monitoring device provided by the invention can be extended by the network interface so as to remotely display the monitor content. The monitor converts the display data and the alarm audio into a protocol packet data, which is sent, remotely processed and recieved by the network interface. Then the data is analyzed in accordance with the procedure specified in FIG. 7, so that interface and alarm audio output are achieved. The operator can select the content to be displayed on the remote drive box.

An alarm audio output function is added to this example with respect to the previous one. The extended display 3 is integrated with an audio input and a speaker, which can be used to display patient's physiological parameters, wavy curve and produce alarm sound. The display content can be set up in this monitor and the alarm audio output can also be set to open or close for this monitor.

The foregoing examples are only the preferred embodiments and they are not intended to limit this invention. It is understood that all changes and modifications made without departing from the spirit and scope of the invention are deemed to be within the protecting scope of the invention.

The invention claimed is:

1. A medical monitoring method integrating central monitoring function, comprising:
displaying a running mode selection menu;
judging user-selected running mode and when a central monitoring server mode is selected, a broadcast order is sent to the network terminal and a correlative data source is searched at the network terminal;
when the correlative data source is found, a data source address is picked up to connect with a terminal of the said address so as to obtain real-time data of said terminal and place the said real-time data in a data bag;
analyzing the real-time data in the data bag to obtain analyzed data information and display information;
displaying the display information in the form of a menu and when one of the data bags is selected, detailed information of the data bag is displayed and the terminal corresponding to the data bag is controlled according to the address information of the said data bag;
wherein control of the terminal corresponding to the data bag includes: sending control instructions to the controlled terminal corresponding to the selected data bag, said controlled terminal responding to the control instructions, acting to obtain result data, and then receiving said result data;
wherein judging the user-selected running mode comprises: when central monitoring server mode is selected, the broadcast order is sent to the network terminal and the correlative data source is searched at the network terminal; when local monitoring mode is selected, a medical monitoring device judges whether the broadcast order is received from the network, and, if so, picks up the original address of the broadcast order, connects with the terminal corresponding to said address according to that address and sends corresponding local data to said terminal, and, if not, reads and displays the local data or when the mixed mode of local monitoring and central monitoring is selected, the medical monitoring device sends the broadcast order to the networked terminal, searches the correlative data source of the terminal on the network and simultaneously judges whether the broadcast order is received from the network.

2. The medical monitoring method integrating central monitoring function according to claim 1, wherein analyzing the real-time data in the data bag to obtain the analyzed data information and display information includes: when the received analyzed data information contains alarm information, the alarm information is carried out for a secondary analysis to obtain specific alarm content, which is to be converted into display information for display and classified according to preset rules; afterwards, the alarm information is processed in a descending order based on classification, and judging whether audio alarm is required, if so, the preset audio data corresponding to the alarm information must be recalled for alarm.

3. The medical monitoring method integrating central monitoring function according to claim 2, wherein when the correlative data source is found, the data source address is picked up to connect with the terminal of said address so as to obtain the real-time data of said terminal and place said real-time data in the data bag, in addition, when the correlative data source is not found, the medical monitoring device indicates that there is no terminal access, resends the broadcast order to the networked terminal and then searches the correlative data source at the network terminal.

4. The medical monitoring method integrating central monitoring function according to claim 3, wherein after the correlative data source is found, the data source address is picked up to connect with the terminal of said address so as to obtain the real-time data of said terminal and place said real-time data in the data bag, the real-time data in the data bag is stored, then analyzed and displayed when review is needed.

5. The medical monitoring method integrating central monitoring function according to claim 4, wherein before the display information is displayed in the form of a menu, the display content must be set up for every display device.

6. A medical monitoring device integrating central monitoring function, comprising:
a monitor, a display device and an interactive network equipment;
wherein the monitor including:
a mode selection unit, used to display a running mode selection menu and select the running mode;
a mode judgment unit, connected with the mode selection unit and used to judge the user-selected running mode such that when central monitoring server mode is selected, a broadcast order is sent to a network terminal and a the correlative data source is searched at the network terminal; when local monitoring mode is selected, the medical monitoring device judges whether the broadcast order is received from the network, and, if so, picks up an original address of the broadcast order, connects with a terminal corresponding to said address according to that address and sends corresponding local data to said terminal, and, if not, reads and displays the local data or when the mixed mode of local monitoring and central monitoring is selected, the medical monitoring device sends the broadcast order to the networked terminal, searches the correlative data source of the terminal on the network and simultaneously judges whether the broadcast order is received from the network;
a data receiving/sending unit, connected with the mode judgment unit and the interactive network equipment; when user selects the central monitoring server mode, the broadcast order is sent to the networked monitor via the interactive network equipment and correlative data source of the monitor is searched on the network;
a monitor connection unit, connected with the data receiving/sending unit and the interactive network equipment; when the correlative data source is found, a data source address is picked up via the interactive network equipment to connect with the monitor of said data source address so as to obtain real-time data of said terminal and place said real-time data in a data bag;
a data analysis unit, connected with the data receiving/sending unit and used to analyze the real-time data in the data bag to obtain the data information and display information;

a monitor selection unit, connected with the display device and used to select a target monitor from a display menu;

a monitor operating unit, connected with the monitor selection unit and the interactive network equipment, and used to send operating instructions to the target monitor via the interactive network equipment;

and the display device connected with the data analysis unit and the monitor selection unit is used to display the display information in the form of a menu, and meanwhile, when user selects the data bag from one of the monitors, the display device will display the detailed information of such data bag.

7. The medical monitoring device integrating central monitoring function according to claim 6, wherein it also comprises a remote drive box which includes:

a data receiving unit, connected with the data analysis unit and used to receive alarm information contained in analyzed data information and display information;

a secondary analytic unit, connected with the data receiving unit and used to analyze the received alarm information to obtain specific alarm content;

an alarm processing unit, connected with the secondary analytic unit; when the specific alarm content is received, the alarm processing unit classifies the alarm information according to preset rules and then sends it to the display device and an alarm judgment unit in a descending order based on classification;

an alarm set up unit, used to set up conditions for audio alarm;

an alarm judgment unit, connected with the alarm processing unit and the alarm setup unit and used to judge whether the alarm information meets the requirements for audio alarm;

an audio alarm unit, connected with the alarm judgment unit and used to recall preset audio data corresponding to the alarm information for alarm when the alarm information meets the requirements for audio alarm.

8. The medical monitoring device integrating central monitoring function according to claim 7, wherein said monitor also comprises:

a measuring unit, used to measure the local data and send the local data to the display device;

a storage unit, connected with the monitor connection unit and the data analysis unit, and used to store real-time data and send the real-time data to the data analysis unit when review is needed;

a display setup unit, connected with the display device and used to set up the display content of the display device; and an alarm unit, connected with the data analysis unit; when the alarm information is detected in the analyzed data information, it recalls the preset audio data corresponding to the alarm information for alarm.

* * * * *